: US006110750A

United States Patent [19]
Sugden et al.

[11] Patent Number: 6,110,750
[45] Date of Patent: *Aug. 29, 2000

[54] **RAPID DETECTION METHOD OF *MYCOBACTERIUM BOVIS* BY FLUORESCENCE POLARIZATION**

[76] Inventors: Edward A. Sugden, 51 Woodmount Crescent, Nepean, Canada, K2E 5P9; Michael E. Jolley, 34469 N. Cir., Round Lake, Ill. 60073; Min Lin, Apt. 5 - 38 Passe Hull, Quebec, Canada, K3E 6P2

[*] Notice: This patent issued on a continued prosecution application filed under 37 CFR 1.53(d), and is subject to the twenty year patent term provisions of 35 U.S.C. 154(a)(2).

[21] Appl. No.: 08/884,579

[22] Filed: Jun. 27, 1997

Related U.S. Application Data

[60] Provisional application No. 60/020,853, Jun. 28, 1996.

[51] Int. Cl.[7] .............................. G01N 33/542; C07K 1/00
[52] U.S. Cl. ......................... 436/537; 436/546; 436/172; 530/350; 530/402; 530/403; 530/820
[58] Field of Search .................... 435/7.1, 975; 436/501, 436/513, 536, 537, 544, 546, 63, 800, 172; 530/350, 820, 402, 403

[56] References Cited

U.S. PATENT DOCUMENTS

| | | |
|---|---|---|
| 4,476,229 | 10/1984 | Fino et al. . |
| 4,492,762 | 1/1985 | Wang et al. . |
| 4,699,512 | 10/1987 | Koshi . |
| 4,751,190 | 6/1988 | Chiapetta et al. . |
| 4,952,691 | 8/1990 | Wang et al. . |
| 5,066,426 | 11/1991 | Wang et al. . |
| 5,070,025 | 12/1991 | Klein et al. . |
| 5,239,057 | 8/1993 | Wang et al. . |
| 5,248,791 | 9/1993 | Brynes et al. . |
| 5,315,015 | 5/1994 | Hui et al. . |
| 5,354,693 | 10/1994 | Brynes et al. . |
| 5,372,949 | 12/1994 | Zeitvogel et al. . |
| 5,391,740 | 2/1995 | Wang et al. . |
| 5,427,960 | 6/1995 | Wang et al. . |
| 5,463,027 | 10/1995 | Wang et al. . |
| 5,614,408 | 3/1997 | Stanker et al. . |
| 5,707,819 | 1/1998 | Wood et al. . |

OTHER PUBLICATIONS

Lin et al, Clinical and Diagnostic Laboratory Immunology, Jul. 1996, 3(4):438–443.

Haugland, R.P., Molecular Probes Handbook of Fluorescent Probes and Research Chemicals 1992–1994 pp. 67–68.

Dandliker et al, Biochem Biophys Res Comm, 5:299–304, 1961.

Dandliker et al, Immunochemistry, 1:165–191, 1961.

*Primary Examiner*—Patricia A. Duffy
*Attorney, Agent, or Firm*—McDonnell Boehnen Hulbert & Berghoff

[57] ABSTRACT

An assay for the detection of antibodies to the MPB70 protein secreted by Mycobacterium bovis utilizes a tracer consisting of the MPB70 protein conjugated to a fluorophore such as fluorescein. Upon mixing with the antibodies specific for MPB70 protein contained in the serum of an animal infected with *M. bovis*, the bound tracer exhibits an increase in fluorescence polarization, detectable in an instrument.

4 Claims, 4 Drawing Sheets

FIG. 2a
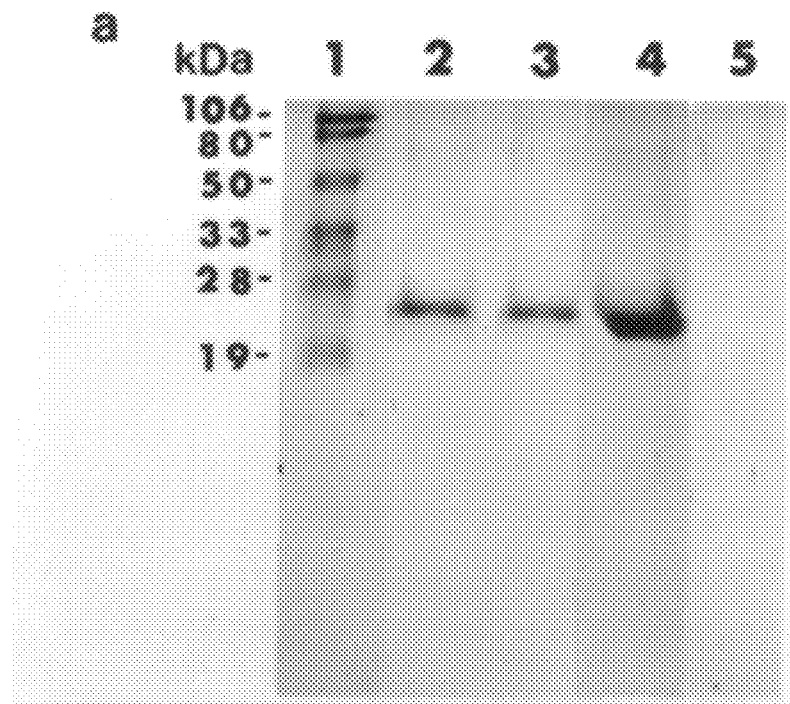
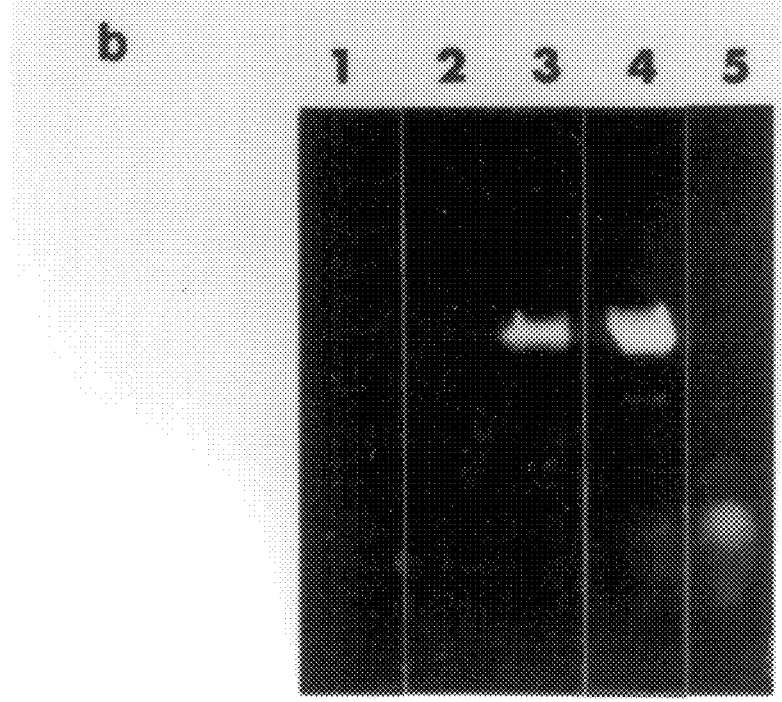
FIG. 2b

RAPID DETECTION METHOD OF *MYCOBACTERIUM BOVIS* BY FLUORESCENCE POLARIZATION

CROSS-REFERENCE TO RELATED APPLICATION

This application is a utility application filed during the copendancy of Provisional application, Ser. No. 60/020,853, filed Jun. 28, 1996.

FIELD OF THE INVENTION

This invention relates to the field of immunoassay, and in particular to the detection of antibodies to antigens specific for infectious disease entities. The subject matter encompasses both tracer reagents for use in fluorescence polarization detection, and in assay configurations.

BACKGROUND OF THE INVENTION

*Mycobacterium bovis* causes infection (tuberculosis) in a variety of farm and wild animals and also humans, Van Emden, et al., Iowa State University Press, Ames, Iowa (1995). This organism along with *M. tuberculosis, M. africanum*, and *M. Microti* belongs to the taxonomically closely related members of *M. tuberculosis* complex. Numerous attempts have been made to seek a species-specific antigen with high sensitivity for diagnosis of *M. bovis* infection. A protein antigen MPB70 is secreted from *M. bovis* cells following cleavage of a 30-amino acid signal peptide which directs active transport of the protein across the cytoplasmic membrane Terasaka, et al., *FEMS Microbiol. Lett.*, 58:273–276 (1989). The protein forms a major component of *M. bovis* culture filtrate, accounting for up to 10% of the protein excreted by some *M. bovis* Bacillus Calmette-Guerin (BCG) strains, Harboe, et al., *Infect. Immun.*, 52:293–302 (1986), and possibly as much as 23%, Abou-Zeid, et al., *J. Gen Microbiol.*, 132:3047–3053 (1986). The function of this protein is unknown.

The protein was first purified to homogeneity from culture filtrates of *M. bovis* BCG by Nagai, et al., *Infect. Immun.*, 31:1152–1160 (1981), and later from culture filtrates of *M. bovis* AN-5 by Fifis, et al. Also, the gene coding *M. bovis* MPB70 has been cloned, sequenced and expressed in *Escherichia coli*, Hewinson, et al., *Scand. J. Immun.*, 26:445–454 (1987). The molecular mass of MPB70 was estimated to be 18–23 kDa by SDS-PAGE, 15 kDa by sedimentation equilibrium analysis, and 16 kDa as deduced from the gene-derived amino acid sequence. The MPB70 protein exists as a glycosylated or non-glycosylated form.

The MPB70 protein is considered to be a highly species-specific immunodominant antigen that contains at least three separate *M. bovis*-specific epitopes, although some cross-reactivity with Nocardia asteroides has been reported. The protein is an active component of purified protein derivative (PPD) tuberculin, Harboe, et al., *J. Clin. Microbiol.*, 28:913–921 (1990), and is able to elicit a delayed-type hypersensitivity response and to stimulate T- and B-lymphocyte responses in *M. bovis*-infected animals. Because of high species-specificity and its immunodominant properties that stimulate antibody production in infected animals, MPB70 has been incorporated into ELISA for detection of anti-MPB70 antibodies which serve as an indicator of *M. bovis* infection.

SUMMARY OF THE INVENTION

It is an object of this invention to provide a simple assay that can rapidly detect anti-MPB70 antibodies in serum. A further object is to develop such an assay using the concept of fluorescence polarization.

According to the present invention, *Mycobacterium bovis* extracellular protein MPB70 is modified with fluorescein or other fluorophore and incubated with sera containing *M. bovis*-specific antibodies. The increase in fluorescence polarization is measured upon the immunospecific binding of protein MPB70 and antibodies specific therefor.

In further detail, the present method comprises diluting in a buffer serum suspected of containing antibodies to *M. bovis* obtained from an animal, such as elk, bison, cattle, llamas, and water buffalo, particularly exotic animal species, reading the sample in an instrument to determine the background degree of fluorescence polarization, adding a tracer consisting of *M. bovis* extracellular protein MPB70 conjugated to a fluorophore to a form a mixture, incubating until equilibrium of binding between antibody and tracer is established, and reading the sample in an instrument to measure the fluorescence polarization value thereof after binding the assay reading is the fluorescence polarization reading after a blank substract.

The present invention also provides a reagent, comprising a tracer for use in a fluorescence polarization assay for antibodies to the MPB70 protein secreted by *M. bovis*, obtained by conjugating a fluorophore to *M. bovis* extracellular MPB70 protein.

*M. bovis*-specific antibodies and an increase in fluorescence polarization of fluorescein-labeled antigen was detected.

Traditionally, the method for detecting antibodies to MPB70 protein with a fluorphore-conjugated purified MPB70 protein antigen to form a mixture, incubating said mixture for a time sufficient to form an immune complex, and measuring the extent of formation of said immune complex by comparing the fluorescence polarization value after complex formation to a negative control value.

BRIEF DESCRIPTION OF THE DRAWINGS

FIG. 2a is a photograph of the SDS-PAGE migration patterns of MPB-70 and its fluorescein-labelled derivative under Coomassie blue staining.

FIG. 2b is a photograph of the same reagents as in 2a, only showing the fluorescent bands.

DESCRIPTION OF THE PREFERRED EMBODIMENT

Figure 1A:
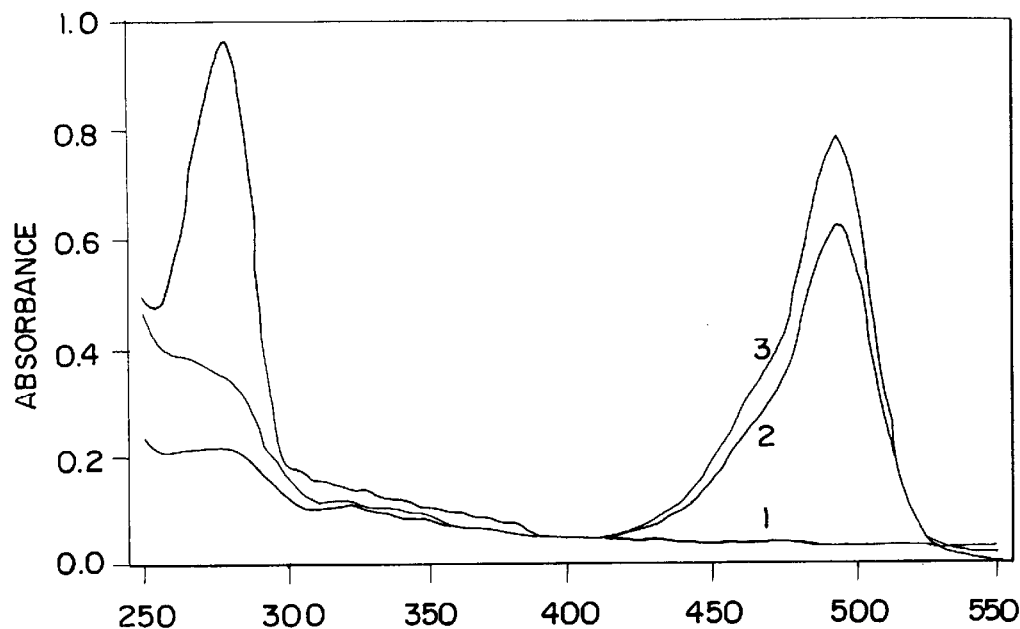
FIG. 1a is a plot of adsorption spectra for fluorescein and the conjugate reagent, FITC.
Figure 1B:
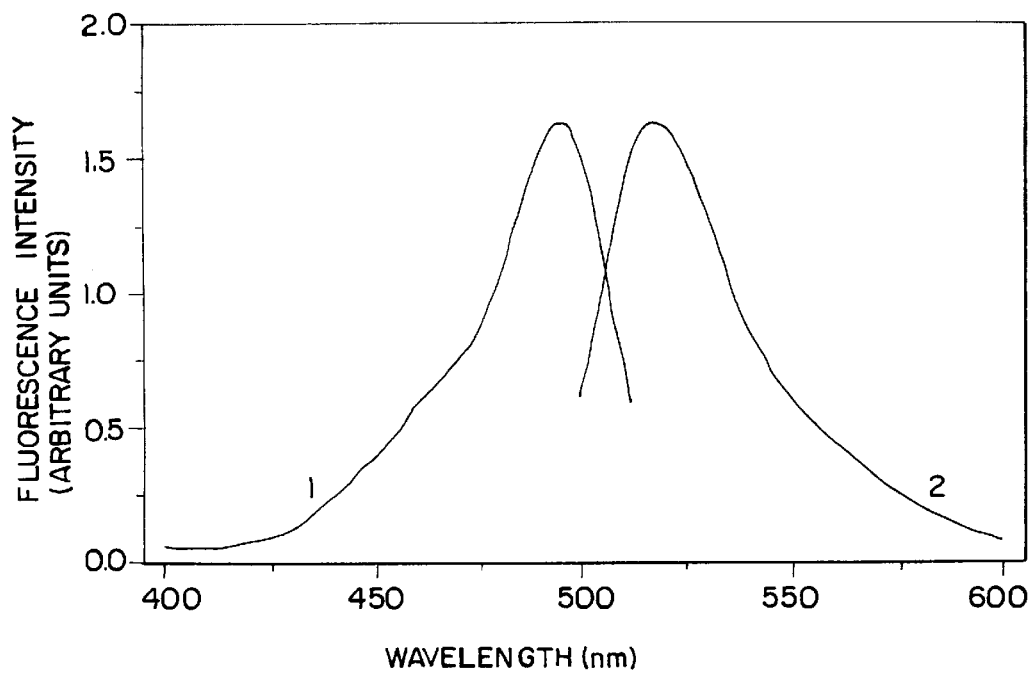
FIG. 1b is a plot of adsorption spectra for fluorescein and the fluorescein-conjugated MPB-70 tracer.
Figures 3A, 3B:
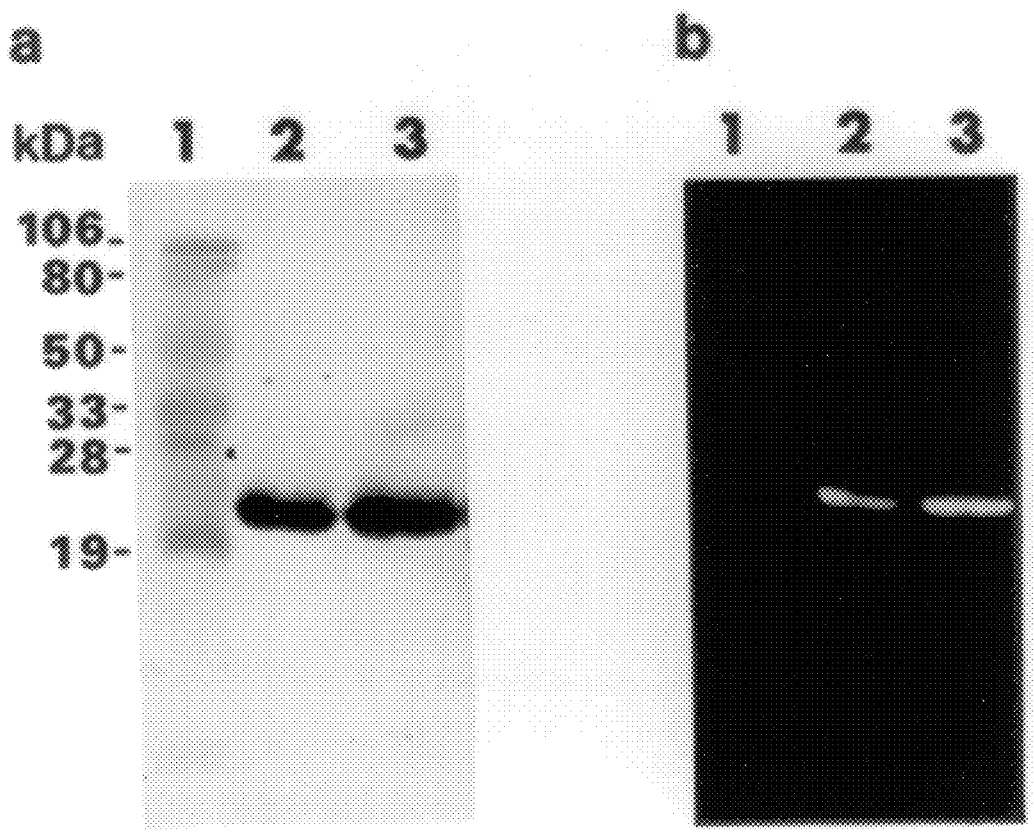
FIGS. 3a and 3b are the corresponding photographs to FIGS. 2a and 2b, for Western blot.
Figure 4A:
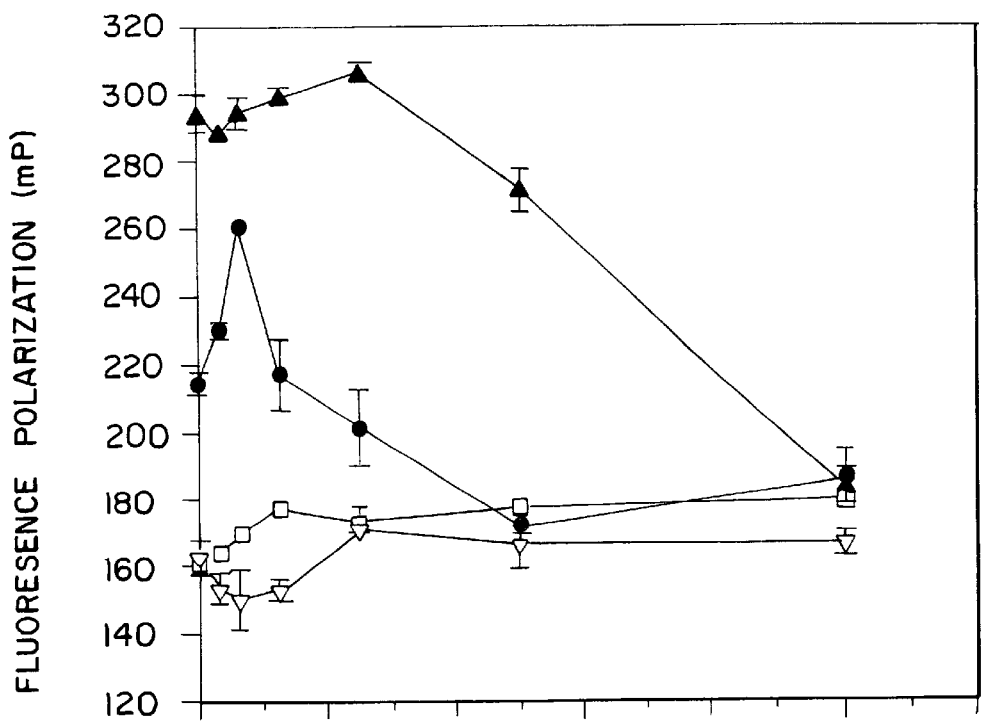
FIG. 4a is a graph showing the relation of fluorescence polarization in mP as a function of LDS concentration.
Figure 4B:
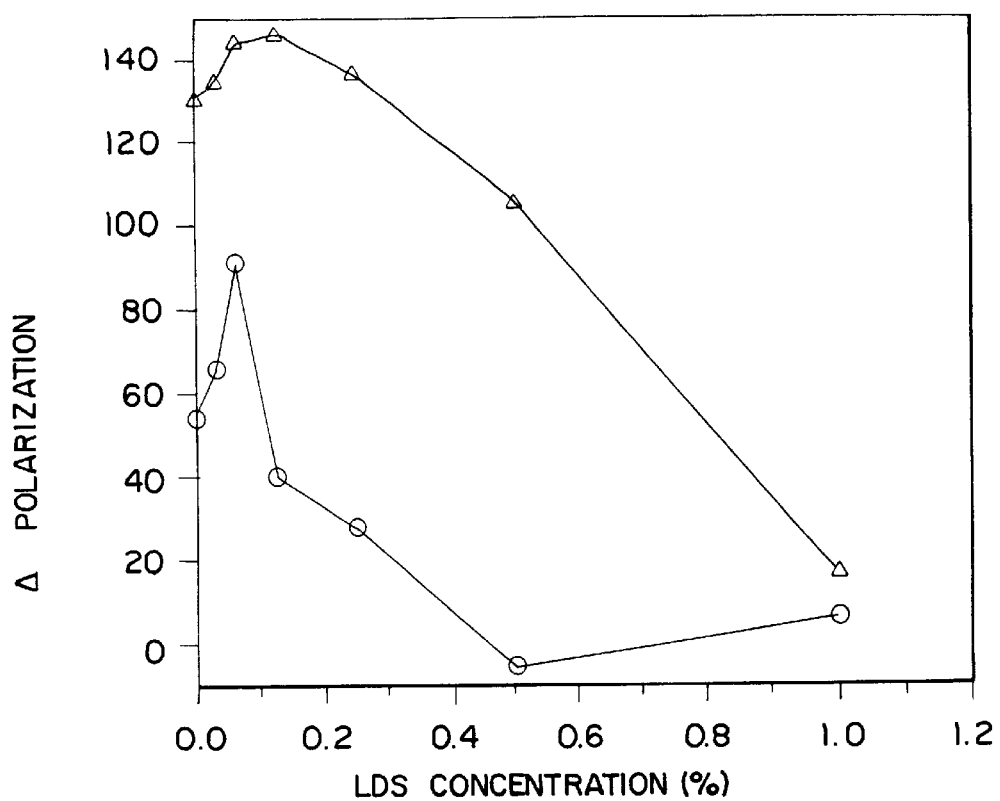
FIG. 4b is a graph of the change in mP as a function of LDS concentration.

The theory of fluorescence polarization was first described in 1926 by Perrin. When fluorescent molecules in solution are excited by a plane-polarization light beam, they emit fluorescence back into the same polarized plane, provided that the molecules remain stationary. However, if the excited molecules rotate or tumble during the excited state, then fluorescence is emitted into a plane different from the plane used for excitation. The degree of fluorescence polarization, P, is defined as:

$$P = \frac{I_v - I_h}{I_v + I_h}$$

where $I_v$ and $I_h$ are the intensities of the vertically and horizontally polarized components of the emitted light, respectively. The polarization of a fluorescent molecule is dependent on its rotational relaxation time ρ and its fluorescence lifetime τ, described by the Perrin equation, Perrin, et al., J. Phys. Radium. 7:390–401 (1926).

$$\left(\frac{1}{P} - \frac{1}{3}\right) = \left(\frac{1}{P_o} - \frac{1}{3}\right)\left(1 + \frac{3\tau}{\rho}\right)$$

where $P_o$ is the limiting polarization of fluorescence.

If τ is constant, the observed polarization is dependent solely on ρ (i.e., the time a molecule takes to rotate through an angle of approximately 65.5°), which is related to the molecular volume (V), the gas constant (R), and the viscosity (η) and absolute temperature (T) of the solution by the Stokes equation:

$$\rho = \frac{3\eta V}{RT}$$

Therefore, if the viscosity and temperature of a solution are held constant, polarization is dependent on the molecular volume, that is, the size of a fluorescent molecule. High polarization values mean that the molecule is large and has rotated very little during the excited state; low values mean that the molecule is small and rotated faster during the excited state. Recently, a fluorescence polarization assay for the detection of antibodies to Brucella abortus in bovine sera has been described, Nielsen, et al., Submitted for publication (1996).

A novel assay of the present invention (FPA) utilizing fluorescein-labeled *Mycobacterium bovis* secretory protein MPB70 for rapid detection of anti-MPB70 antibodies in selected sera from three *M. bovis*-infected species (elk, llamas and bison). The test has been found to be particularly efficacious for exotic animal species, defined generally as wild animal species of mammal, or domestic species not ordinarily used for human food. Labeling of purified MPB70 with fluorescein isothiocyanate resulted in incorporation of 0.96±0.08 (Mean±SD, n=3) fluorescein groups per MPB70 molecule. The labeled protein fluoresced strongly with an emission maximum at 518 nm when excited with light of a wavelength near 493 nm, and its immunoreactivity with anti-MPB70 monoclonal antibody 4C3/17 was not altered by modification with fluorescein. The FPA protocol was optimized for analysis of serum samples by incorporation of 0.05% lithium dodecyl sulfate into the assay buffer which eliminates some possible non-specific interactions.

Sera from *M. bovis*-infected animals, selected on the basis of exhibiting the presence of anti-MPB70 antibodies by ELISA, reacted with fluorescein-labeled MPB70 resulting in an increase in polarization up to 330 milli-polarization units (mP), in contrast to values (167–178 mP) for non-infected sera which were close to that (164.7±3.3 mP, n=6) in the absence of specific antibodies. These results demonstrated that fluorescein-labeled MPB70 can be used as a tracer to detect anti-MPB70 antibodies.

The fluorophore-labelled MPB-70 tracer of the present invention contains 1–3 fluorophore groups per MPB70 molecule. Care must be taken not to over label the target antigen, so as to cause steric hinderance of antibody and antigen binding. Further, the tracer must be purified to electrophoretic homogeneity, and be at least 95% pure with respect to contaminating proteins. The fluorophore, which may be selected from fluorescein, rhodamine, BODIPY™ (4,4-difluoro-4-bora-3a,4a-diaza-s-indacene), TEXAS RED™ (isomeric sulfonyl chlorides of sulforhodamine 101), or LUCIFER YELLOW™ (1H-Benze[de]isoquinoline-5,8-disulfonic acid, 6-amino-2-2,3-dihydro-1,3-dioxo-, dilithium salt), but preferably fluorescein, is conjugated to the MPB70 protein, by conventional chemistries.

EXAMPLE I

Chemicals. Fluorescein isothicyanate (FITC) isomer I, 2,2'-azino-bis(3-ethylbenzthiazoline-6-sulfonic acid) (ABTS), and lithium dodecyl sulfate (LDS) were purchased from Sigma (St. Louis, Mo., USA). Protein markers (prestained), nitroblue tetrazolium, and 5-bromo-4-chloro-3-indolyl phosphate were obtained from Bio-Rad (Richmond, Calif., USA) and Sephadex G-25 was obtained from Phamacia Biotech Canada (Baie D'Urfe, Quebec). Peroxidase-labeled streptavidin, and biotin-protein G were purchased from Kirkegaard & Perry Laboratories, Inc. (Gaithersburg, Md., USA) and alkaline phosphate conjugated goat anti-mouse IgG was obtained from ZYMED Laboratories, Inc. (So. San Francisco, Calif., USA). A bicinchoninic acid (BCA) protein assay kit was purchased from Pierce (Rockford, Ill., USA) and murine monoclonal antibody to MPB70 (4C3/17), originally developed by Wood, et al., *J. Gen. Microbiol.*, 134:2599–2604 (1988), was obtained from Agen Biomedical Limited Inc. (Acacia Ridge, Queensland, Australia).

Fluorescein labeling of MPB70 form *Mycobacterium bovis* BCG. MPB70 was purified to homogeneity from culture filtrates of *Mycobacterium bovis* BCG Tokyo by chromatofocusing, lectin affinity and hydrophobic interaction chromatography. Lyophilized MPB70 (1 mg) was dissolved in 0.5 ml of 0.85% saline, mixed with 0.15 ml of 1 mg/ml FITC in 0.15 M Na$_2$HPO$_4$-NaOH (pH 9.5), and then incubated at 37° C. for 1 hr. Following the incubation, the reaction mixture was immediately applied, at 0.5 ml/min, to a column of Sephadex G-25 (1×23 cm) pre-equilibrated with 0.1 M Na$_2$HPO-NaH$_2$PO4 buffer (pH 7.0) containing 0.04% NaN$_3$. The absorbance was monitored at 492 nm, and fractions of 0.5 ml collected. The elution profile showed two well-separated peaks. The first peak contained fluorescein-labeled MPB70. Fractions of this peak were pooled and stored at 4° C.

The degree of incorporation of fluorescein groups into MPB70 was determined by independent measurements of the concentrations of FITC and protein in a given sample. The FITC concentration was estimated spectrophotometrically, taking the molar absorption coefficient to be 7.45×10$^4$ M$^{-1}$ cm$^{-1}$, Bernnardt, *Biochem. Biophys.* Acta, 745:140–148 (1983). The concentration of MPB70 in this sample was determined by the calorimetric method, Smith, et al., *Anal. Biochem.*, 150:76–85 (1985), using a bicinchoninic acid protein assay kit (Pierce) and BSA as standard.

SDS-PAGE and Western blotting. Sodium dodecyl sulfate polyacrylamide gel electrophoresis (SDS-PAGE) was carried out by the method of Laemmli, Laemmli, et al., *Nature*, 227:680–685 (1970), with 4% stacking gels and 12% resolving gels using a Bio-Rad mini-gel apparatus. The separated proteins were either stained with Coomassie blue or electroblotted onto a nitrocellulose membrane using a Bio-Rad Trans-Blot SD semi-dry transfer cell. The nitrocellulose membrane using a Bio-Rad Trans-Blot SD semi-dry transfer cell. The nitrocellulose membrane was blocked with 3% skim milk powder in PBS containing 0.05% Tween-20 (PBS-T) for 1.5 hr and then incubated at room temperature for 2 hr with murine monoclonal antibody 4C3/17 at a 1:5000 dilution in PBS-T containing 3% BSA. Bound antibodies were detected by alkaline phosphatase conjugated goat anti-mouse IgG at a 1:1000 dilution in PBS-T containing 3% BSA using nitroblue tetrazolium and 5-bromo-4-chloro-3-indolyl phosphate as substrates, Lin, et al., *Arch. Biochem. Biophys.*, 269:219–227 (1989).

EXAMPLE II

A number of *M. bovis*-infected and non-infected elk (n=9), llamas (n=9) and bison (n=9) field serum samples were used in the present study for investigating fluorescein-labeled MPB70 as a potential probe to detect specific antibodies by fluorescence polarization. Sera were selected on the basis of an enzyme-linked immunosorbent assay (ELISA) described below, including representatives from non-infected animals with $A_{405}$ values similar to that obtained with PBS (<0.09) and from infected animals (llamas were post-skin test) with $A_{405}$ values at least 2-fold greater than 0.09 (Table 1).

ELISA for antibodies to MBP70. Microtiter plates were coated overnight at room temperature with purified MBP70 at 1 $\mu$g/ml in 50 mM carbonate buffer (pH 9.5, 100 $\mu$l/well). The plates were washed with PBS-T, blocked with PBS containing 3% gelatin for 1.5 hr, and then incubated with sera (1:50 or 1:500 dilution in PBS-T, 100 $\mu$l/well) at 37° C. for 1.5 hr. The plates were washed with PBS-T followed by incubation with biotin-protein G (1:5000 dilution in PBS-T 100 $\mu$l/well) at 37° C. for 1 hr. The plates were washed with PBS-T, and streptavidin-horseradish peroxidase conjugate (1:5000 dilution in PBS-T, 100 $\mu$l/well) was added for 1 hr at 37° C. After a final washing with PBS-T, citric acid buffer (50 mM, pH 4.5; 200 $\mu$l/well) containing ABTS (1 mM) and $H_2O_2$ (0.02%) was added into the wells. Following incubation with shaking at room temperature for 10 min, the absorbance at 405 nm ($A_{405}$) was determined using a Titertek plus MS2 Reader (ICN Flow, AL, USA).

Fluorescence polarization assay (FPA) for antibodies to MPB70. Serum samples were diluted 50-fold in 10 mM PBS containing 0.05% LDS and 0.1% $NaN_3$ (total volume=2 ml). To diluted serum was added 20 $\mu$l of $2.5\times10^{-4}$ $\mu$M fluorescein-labeled MPB70. After incubation at room temperature for 10 min (steady-state polarization was achieved within 2 min), fluorescence polarization was measured using a FPM-1 Fluorescence polarization analyzer (Jolley Consulting and Research, Inc., Round Lake, Ill., USA), the characteristics and use of which, has been described, Jolley, et al., *J. Anal. Toxicol.*, 5:236–240 (1981). Blank fluorescence polarization was determined prior to adding fluorescein-labeled MPB70. The observed polarization is expressed in terms of milli-polarization units (mP).

Spectroscopic methods. A Phamacia LKB spectrophotometer (Ultrospec plus) was used to measure 4 absorbance. A SLM-Aminco Model 8000C spectrofluorometer equipped with an IBM microcomputer and a circulating water bath was used for determination of fluorescence excitation and emission spectra. Excitation and emission bandpasses were 8 nm. Excitation and emission wavelengths were 490 nm and 520 nm, respectively. Spectra were smoothed using the SLM data manipulation software.

EXAMPLE III

Characterization of fluorescein-labeled MPB70. Reaction between MPB70 and FITC resulted in a covalent attachment of fluorescein groups to MPB70, as indicated by absorption spectrum of fluorescein-labeled MPB70 which shows an absorbance maximum at 493 nm resembling that of FITC (FIG. 1*a*). The labeled protein shows a similar fluorescence spectrum of fluorescein with excitation and emission maximum at 493 nm and 518 nm, respectively (FIG. 1*b*). Incorporation of FITC into MPB70 was confirmed by SDS-PAGE (FIG. 2). The samples containing fluorescein-labeled MPB70 migrated to a position corresponding to the unmodified MPB70 on the Coomassie blue stained gel (FIG. 2*a*) and displayed corresponding fluorescent bands in the photograph of the gel taken under ultraviolet illumination prior to staining (FIG. 2*b*). Under the reaction conditions employed (mole ratio of FITC to MPB70=8:1, 37° C. for 1 hr), the degree of modification was quantitated to be 0.96±0.08 (Mean±SD, n=3) mol FITC/mol MPB70. At the concentration used in FPA, fluorescein-labeled MPB70 showed a fluorescence polarization value of 164.7±3.3 mP (n=6) in PBS.

To determine whether modification with FITC altered the structural integrity of the 4C3/17-defined epitope, fluorescein-labeled MPB70 was analyzed by Western blotting (FIG. 3). The reaction between (FIG. 3*a*) which has a corresponding fluorescent band in the photograph of the gel taken under ultraviolet illumination prior to electroblotting (FIG. 3*b*).

Effect of LDS on FPA. A detergent, lithium dodecyl sulfate (LDS), was used in the FPA buffer to prevent possible non-specific interactions between fluorescein-labeled MPB70 and other serum components. To establish an optimal concentration of LDS for use in the assay, fluorescence polarization after mixing the labeled MPB70 with serum either from an infected or from a non-infected elk was investigated as a function of LDS concentration. The results are shown in FIG. 4*a*. For the serum from an infected animal (1:10 dilution), fluorescence polarization increased slightly in response to the increase in LDS concentration up to 0.3% and decreased dramatically afterwards. For the same serum at a dilution of 1:50, fluorescence polarization increased sharply when LDS concentration varied from 0 to 0.06% and decreased rapidly beyond this concentration range. As a negative control, fluorescence polarization for the serum from a non-infected elk was also examined as a function of LDS concentration. Polarization for this serum at a dilution of 1:10 decreased slightly from 160 to 150 mP when LDS concentration varied from 0 to 0.12% and then increased up to 170 mP at LDS concentration greater than 0.12%. The variation of LDS concentration between 0 and 1% also slightly increased fluorescence polarization from 160 to plateau value of about 180 mP for the serum from the non-infected elk at a 1:50 dilution. The optimal concentration of LDS for use in the assay buffer was determined as the one that gives the greatest polarization difference between the sera from the infected and non-infected elks (FIG. 4*b*). As shown in FIG. 4*b*, the optimal concentration of LDS was about 0.05% for a serum dilution form 1:10 to 1:50, and a higher LDS concentration (0.1%) may be used with a lower dilution of serum (1:10).

Detection of serum antibodies to MPB70 by fluorescence polarization. Nine sera from each of three species (elk, llamas and bison), six from infected and three from non-infected animals based on the cultural isolation of *M. bovis* from tissues (Table 1), were selected for the presence or absence of anti-MPB70 antibodies by ELISA with purified MPB70 on the solid-phase. The ELISA results are shown in Table 1. Six sera from non-infected representatives of each species were chosen each with an $A_{405}$ value similar to that obtained with PBS (<0.09), indicating the absence of anti-MPB70 antibodies; three sera from infected representatives of each species were chosen each with an $A_{405}$ value 2–30 fold greater than 0.09, indicating the presence of anti-MPB70 antibodies. These sera were further analyzed by fluorescence polarization using fluorescein-labeled MPB70 as a probe. As shown in Table 1, all the sera from non-infected animals gave polarization values between 167 to 178 mP, which are similar to the value of 164.7±3.3 (Mean±SD, n=6) in the absence of specific antibodies (i.e., in PBS). However, the reaction between fluorescein-labeled MPB70 and the sera from infected animals resulted in higher values of fluorescence polarization ranging from 203 to 330 mP (Table 1). These results were in good agreement with the ELISA data, and demonstrated the feasibility fusing fluorescein-labeled MPB70 to detect anti-MPB70 antibodies by fluorescence polarization.

No previous reports are available on the use of fluorescence polarization in detecting specific antibodies in animals with mycobacterial infection, although some preliminary work has shown a detection of antibodies to mycobacteria using non-specific fluorescein-labeled arabinomannan. Herein, the non-glycosylated form of MPB70 was covalently conjugated with fluorescein groups for use as a probe to detect anti-MPB70 antibodies using selected sera from three *M. bovis*-infected species (elk, llamas and bison) as a model. Labeling of MPB70 did not interfere with its immunoreactivity with anti-MPB70 monoclonal antibody 4C3/17.

In this study, 27 animals from three species were classified as infected (3 per species) and non-infected (6 per species) on the basis of cultural isolation of *M. bovis* from tissues. This microbiological procedure is generally considered to be the "gold standard" and the definitive test for the confirmation of *M. bovis* infection. The MPB70-based ELISA was performed to select *M. bovis*-infected animals with anti-MPB70 antibodies and non-infected animals without these antibodies (Table 1). The FPA described here was also able to detect anti-MPB70 antibodies in the sera from infected but not non-infected animals, as revealed by the fact that (i) the polarization values for the sera from infected animals were greater than those from non-infected animals and (ii) the values for the latter sera were very close to that in the absence of specific antibodies (i.e., in PBS). A detergent LDS at the optimal concentration was included in the assay buffer, and presumably this would eliminate some of the possible non-specific binding of other serum components to the fluorescein-labeled antigen.

The FPA results are in good agreement with those obtained with ELISA, demonstrating the feasibility of the former assay as an alternative antibody assay to ELISA or other antibody assay systems. It may be expected that the assay described in this study offers the same or similar kind of specificity and sensitivity for detection of *M. bovis*-infected animals as compared to the MPB70-based ELISA because both assays are essentially designed for targeting the same antibodies. The FPA has several advantages over the ELISA or other antibody assay systems including: (i) polarization measurements are carried out in a single-phase reaction mixture (homogeneous assay); (ii) no separation and washing steps are necessary; (iii) measurements are simple and fast, and the results can be obtained within a few minutes (2 minutes in the present study); (iv) it is very economical and may be performed outside the laboratory. Thus, the FPA may be useful in epidemiological surveys. The speed of this assay should be very attractive in a field situation where the diagnostic results must be obtained in a very short period of time. Also, the concept of this novel immunoassay should have a general applicability to diagnosis of other infectious diseases especially where the causative agents normally cause an antibody response in the host and the demonstration of such a response is an indicator of infection.

TABLE 1

DETECTION OF ANTI-MPB70 ANTIBODIES BY FPA

| Serum Source | Cultural Isolation | ELISA ($A_{405}$) (1:500 dilution) | Fluorescence Polarization (mP) (1:50 dilution) |
|---|---|---|---|
| Elk | | | |
| 1 | −[a] | 0.009 ± 0.001[d] | 169.6 ± 0.7 |
| 2 | − | 0.014 ± 0.003 | 168.9 ± 0.4 |
| 3 | − | 0.012 ± 0.002 | 169.6 ± 0.9 |
| 4 | − | 0.008 ± 0.004 | 170.2 ± 0.4 |
| 5 | − | 0.040 ± 0.005 | 169.6 ± 2.9 |
| 6 | − | 0.062 ± 0.014 | 169.4 ± 0.9 |
| 7 | +[b] | 0.375 ± 0.029 | 279.9 ± 0.7 |
| 8 | + | 0.196 ± 0.006 | 227.1 ± 1.0 |
| 9 | + | 1.198 ± 0.211 | 247.9 ± 5.1 |
| Llamas[c] | | (1:500 dilution) | (1:50 dilution) |
| 1 | − | 0.008 ± 0.003 | 171.2 ± 1.0 |
| 2 | − | 0.010 ± 0.004 | 170.5 ± 1.8 |
| 3 | − | 0.007 ± 0.003 | 177.8 ± 2.0 |
| 4 | − | 0.005 ± 0.003 | 170.2 ± 0.7 |
| 5 | − | 0.036 ± 0.004 | 169.8 ± 0.9 |
| 6 | − | 0.032 ± 0.025 | 168.1 ± 2.2 |
| 7 | + | 2.670 ± 0.027 | 329.4 ± 0.3 |
| 8 | + | 2.789 ± 0.042 | 314.6 ± 1.2 |
| 9 | + | 2.687 ± 0.115 | 299.6 ± 0.5 |
| Bison | | (1:50 dilution) | (1:50 dilution) |
| 1 | − | 0.031 ± 0.002 | 172.0 ± 1.5 |
| 2 | − | 0.023 ± 0.003 | 169.6 ± 1.6 |
| 3 | − | 0.024 ± 0.005 | 167.0 ± 1.0 |
| 4 | − | 0.089 ± 0.007 | 171.8 ± 0.8 |
| 5 | − | 0.040 ± 0.001 | 169.6 ± 3.3 |
| 6 | − | 0.057 ± 0.006 | 167.9 ± 0.4 |
| 7 | + | 3.212 ± 0.099 | 232.8 ± 1.3 |
| 8 | + | 1.658 ± 0.241 | 221.6 ± 1.1 |
| 9 | + | 1.118 ± 0.113 | 203.5 ± 0.8 |

[a]Negative;
[b]Positive;
[c]Data are presented as the means ± SD (n = 3).

What is claimed is:

1. An assay for detection of *M. bovis*-infected animals comprising the steps of:
    adding to a serum sample from an animal a tracer comprising *M. bovis* extracellular protein MPB70 conjugated to few enough fluorophore molecules per MPB70 protein molecule to avoid steric hindrance of antibody binding to form a mixture; and
    reading the mixture in an instrument to determine a measured fluorescence polarization compared to background florescence polarization, wherein said assay is deemed to be positive if said measured fluorescence polarization exceeds a predetermined value.

2. The assay of claim 1, wherein said serum sample comprises serum from the blood of species comprising bovine, bison, llama, and elk.

3. A tracer for use in a fluorescence polarization assay for antibodies specific for MPB70 protein molecules secreted by *M. bovis*, said tracer comprising:
    fluorophore molecules conjugated to said MPB70 protein molecules at few enough sites to avoid steric hindrance of antibody binding, wherein said tracer is able to bind to said antibodies to produce a detectable change in fluorescence polarization.

4. The tracer of claim 3 wherein said fluorophore is selected from the group consisting of fluoroscein, rhodamine, BODIPY™, TEXAS RED™, and LUCIFER YELLOW™.

* * * * *